United States Patent
Tepic

(10) Patent No.: US 11,202,711 B2
(45) Date of Patent: Dec. 21, 2021

(54) PARTIAL HIP PROSTHESIS

(71) Applicant: Slobodan Tepic, Zurich (CH)

(72) Inventor: Slobodan Tepic, Zurich (CH)

(73) Assignee: Scyon Orthopaedics AG, Zürich (CH)

( * ) Notice: Subject to any disclaimer, the term of this patent is extended or adjusted under 35 U.S.C. 154(b) by 0 days.

(21) Appl. No.: 15/189,301

(22) Filed: Jun. 22, 2016

(65) Prior Publication Data

US 2016/0374813 A1    Dec. 29, 2016

Related U.S. Application Data

(63) Continuation of application No. 13/516,821, filed as application No. PCT/EP2010/069977 on Dec. 16, 2010, now abandoned.

(30) Foreign Application Priority Data

Dec. 16, 2009   (EP) ..................................... 09179497

(51) Int. Cl.
     *A61F 2/32*        (2006.01)
     *A61F 2/36*        (2006.01)
     (Continued)

(52) U.S. Cl.
     CPC ........ *A61F 2/3601* (2013.01); *A61B 17/1668* (2013.01); *A61F 2/3603* (2013.01);
     (Continued)

(58) Field of Classification Search
     CPC .................. A61F 2/3601; A61F 2/4607; A61F 2002/30581; A61F 2002/30673;
     (Continued)

(56) References Cited

U.S. PATENT DOCUMENTS 3,412,733 A   *   11/1968   Ross .................. A61B 17/1666
                                               408/223
4,170,794 A      10/1979   Zeibig et al.
(Continued)

FOREIGN PATENT DOCUMENTS

CN         101400322 A      4/2009
DE         30 6 178 A1       7/1981
(Continued)

OTHER PUBLICATIONS

Han-Shan et al., "Present Conditions and Prospects of Surface Engineering of Artificial Articulation Material", Surface Engineering of China, vol. 21, No. 5, Oct. 2008, pp. 7-10.
(Continued)

*Primary Examiner* — Christopher D. Prone
(74) *Attorney, Agent, or Firm* — Rothwell, Figg, Ernst & Manbeck, P.C.

(57) ABSTRACT

A partial hip prosthesis for reducing friction and wear in partial hip prosthesis by combining optimized geometry of the articulation and surface treatment of the prosthetic component. In the prosthesis, one of the articulating surfaces—either that of the reamed acetabulum, or that of the femoral head prosthesis is a-spherical so that a fluid-filled gap is formed at the area of major load transfer. The fluid-filled gap is sealed by an annular area of contact, over which the concave and the convex components are congruent. A prosthetic head is fixed to the femur by either a conventional stem, a perforated shell, or a femoral neck prosthesis screwed onto the femur so that it is partially covered by bone and partially exposed on the medial-inferior aspect, where it abuts the reamed cortex of the calcar region.

5 Claims, 14 Drawing Sheets

(51) Int. Cl.
 *A61B 17/16* (2006.01)
 *A61F 2/30* (2006.01)
 *A61F 2/46* (2006.01)
(52) U.S. Cl.
 CPC ..... *A61F 2/4607* (2013.01); *A61F 2002/3085* (2013.01); *A61F 2002/30327* (2013.01); *A61F 2002/30332* (2013.01); *A61F 2002/30354* (2013.01); *A61F 2002/30581* (2013.01); *A61F 2002/30593* (2013.01); *A61F 2002/30673* (2013.01); *A61F 2002/30738* (2013.01); *A61F 2002/30909* (2013.01); *A61F 2002/30934* (2013.01); *A61F 2002/365* (2013.01); *A61F 2002/3623* (2013.01); *A61F 2220/0033* (2013.01); *A61F 2250/0039* (2013.01); *A61F 2310/0058* (2013.01)
(58) Field of Classification Search
 CPC ............... A61F 2002/3623; A61F 2/36; A61F 2002/30354; A61F 2002/365; A61B 17/8847; A61B 17/1637; A61B 17/1668; A61B 17/1684
 See application file for complete search history.

(56) References Cited

U.S. PATENT DOCUMENTS

| | | | |
|---|---|---|---|
| 4,224,699 A | 9/1980 | Weber | |
| 4,328,593 A | 5/1982 | Sutter et al. | |
| 6,284,002 B1 * | 9/2001 | Sotereanos | A61B 17/1753 623/23.27 |
| 6,800,095 B1 * | 10/2004 | Pope | A61F 2/30767 428/212 |
| 7,621,962 B2 | 11/2009 | Lakin | |
| 7,632,276 B2 * | 12/2009 | Fishbein | A61B 17/1666 606/79 |
| 2002/0072805 A1 | 6/2002 | Sullivan et al. | |
| 2004/0243246 A1 | 12/2004 | Philip | |
| 2006/0259148 A1 | 11/2006 | Bar-Ziv | |

FOREIGN PATENT DOCUMENTS

| | | |
|---|---|---|
| DE | 101 11 984 C1 | 8/2002 |
| DE | 10 2005 056509 A1 | 5/2007 |
| EP | 1413263 A1 | 4/2004 |
| EP | 1566154 A1 | 8/2005 |
| WO | 0062718 A1 | 10/2000 |
| WO | 2008058756 A2 | 5/2008 |

OTHER PUBLICATIONS

Zhenghong et al., "Surface Modification of Titanium Alloy for Surgical Implant", Rare Metal, vol. 27, No. 4, Jul. 2003, pp. 11-24.
Text Portion of the Notification of the Third Office Action cited in Chinese Application No. 201080061820.1 dated Jul. 10, 2015, 4 pages.
Indian Application No. 1444/KOLNP/2012 dated Dec. 20, 2018, 6 pages.

* cited by examiner

PARTIAL HIP PROSTHESIS

This application is a continuation of U.S. Ser. No. 13/516,821, filed on Nov. 16, 2012, which is a 35 U.S.C. 371 National Phase Entry Application from PCT/EP2010/069977, filed Dec. 16, 2010, which claims the benefit of European Patent Application No. 09179497.4 filed on Dec. 16, 2009, the disclosures of which are incorporated herein in their entirety by reference.

BACKGROUND

1. Field of the Invention

The invention relates to partial hip joint prostheses. More particularly, it relates to a hip prosthesis comprising a prosthesis for the head of the femur intended to articulate against the reamed bone of the pelvis, wherein the shape of the articulation is such that only an annular contact is possible. The prosthetic head is coated with a friction—reducing coating such as amorphous diamond-like coating. The head is affixed to the femur by attaching it to either the bone of the femoral head, the femoral neck or the shaft of the femur.

2. Discussion of Related Art

Currently used prostheses of the hip joint are either total hip prostheses, wherein joint articulation occurs between a femoral component and an acetabular component of the prosthesis, or partial hip prostheses, wherein only the femoral side is replaced and articulated against the natural acetabulum. The latter are performed almost exclusively for older patients with femoral neck fractures, mostly due to trauma, and can only be used if the acetabulum is still covered by cartilage.

Both types are generally performing satisfactorily, but both are also leading to a number of complications which can be attributed to sub-optimal performance of either the articulation itself or fixation to the bone.

Wear of the materials used for articulation in the total hip replacement often leads to biological sequelae that may require a revision surgery with new implants.

Wear of Ultra High Molecular Weight Polyethylene (UHMWPE), still the most commonly used articulation material, is considered a major contributing factor to aseptic loosening and thus limiting the duration of artificial joints. Reduction of UHMWPE wear has been an important topic of research and development since the sixties, with increased urgency accorded to the problem in the last decade.

Four decades after its introduction into total joint replacement by Chamley, UHMWPE remains the most commonly used material for the concave part of the artificial joints, e.g. for the acetabular cup of the total hip prosthesis, or the tibial plateau of the total knee prosthesis. While it has played a central role in the success and widespread use of joint replacements, UHMWPE has been identified as a major culprit in the most common mode of their failure—aseptic loosening. Wear particles produced by articulation of the hard, convex, metallic, or ceramic component against the soft polymer liner accumulate in and around the joint until the concentration of particles becomes so high that, in spite of the polymer's generally excellent biocompatibility when in bulk, they initiate a biological response leading ultimately to bone loss, loosening of the joint components and dysfunction of the joint replacement.

Different methods of wear reduction have been sought, found and introduced into clinical use over the last few decades, all focused on improving the wear characteristics of the articulation pair at their interface.

On the convex, metallic, or ceramic component these efforts included reducing roughness of the surface, increasing precision of the geometry, e.g. sphericity of the femoral head, and increasing hardness of the materials. Improved wetting of the hard surface has also been identified as an important factor in general wear reduction.

These measures have been realized through: (1) better selection of and processing of metals, in both metallurgical aspects and machining methods; (ii) use of hard coatings, added or created in situ, e.g. by oxidation; (iii) use of bulk ceramic components.

The reduction of wear, both in laboratory testing and from in vivo observations is on the order of factor two.

More recently, modifications of UHMWPE material through cross-linking have gained much attention. Cross-linking can be achieved by physical (irradiation) and/or chemical means. Laboratory testing has shown great variability, mostly due to the different methods of wear production and assessment employed. Tests, conducted on joint simulators and with careful compensation for artifacts, suggest factor five to ten reduction of wear vs. regular UHMWPE.

A number of potential problems of cross-linking have been mentioned in, at present, vast literature on the subject. Among them is the reduction of strength, particularly in fatigue; reduction of average particle size, making the wear debris biologically more active; and risk of long term degradation in the body.

Cross-linked UHMWPE has been in broad clinical use for about five years—too short a time for the final judgment on its benefit-to-risk ratio. Several clinical observations suggest actual wear reduction of about factor two, but again, there is much variability in methods used to assess the wear and thus in the reported results.

Metal-metal articulations had been used prior to the introduction of UHMWPE in the sixties, which has since dominated clinical use. As the biological problems of UHMWPE wear surfaced in the eighties, metal-metal was re-introduced, with better metallurgical and manufacturing technologies available promising better clinical outcomes. The wear rates, compared to UHMWPE, are on the order of factor ten lower by weight; hundred times by volume. However, systemic accumulation of ions of potentially harmful metals has been observed, and the risks remain unknown, especially in younger patients, who are most in need of improved joint replacements.

Ceramic-ceramic articulations are technically the best in terms of wear, but various regulatory obstacles and high prices have, until recently, kept their use to a small percentage of the total. There are also risks, if relatively low, of component breakage due to the extreme brittleness of ceramics and rapid degradation of the articulation caused by minuscule imperfections of, or damage to the surfaces. Sophisticated technologies and quality controls required in production have also been an impediment to their wider use. More recently, ceramic-ceramic articulations have seen another major setback in clinical acceptance, when a significant number of them were found to produce a squeaking noise with every step of the patient.

CH449173, "Gelenkprothese", by Maurice Mueller, discloses a metal on metal prosthesis, whereby the contact is limited to polymeric pads seated into their recesses within the cup.

DE4423020, "Gelenkprothese", by Wolfgang Fitz, discloses a hip prosthesis cup with a reservoir for the lubricating fluid in the unloaded, inferior region, combined with grooves, known in general art of sliding bearings as advantageous, because wear particles are more readily removed from the articulation.

PE19604458, "Gelenkpfanne", by Hagen Seifert, discloses a cup of the hip prosthesis shaped to make contact to the head entirely on a ring near the equator, leaving a spherically shaped recess in the cup filled with fluid, enabled by grooves in the contact area, acting as a shock absorber. Controlling the stiffness of the cup, there are a number of ring shaped cavities within the cup wall. The concept is essentially one of a hydrodynamic bearing. Devoid of fluid support (as would happen in any case if the loading persisted long enough, e.g. fractions of a second) it would either result in very high friction torque, if the load were to be supported by the near-equator contact zone, or it would be reduced to a standard bearing (plus the friction at the contact zone) if the head fell into the recess.

DE19915814, "Gelenk-Endoprothese mit verschleissarmer Gleitpaarung", by Manek Buttermilch, et al., discloses a ceramic-ceramic total hip prosthesis, whereby the contact between the two articulating components is a line contact, achieved by either modified head or cup geometry. In both cases a mismatch is produced by replacing a single radius of curvature with two, with offset centers, resulting in a line contact. Herzian stresses are reduced, but not eliminated. Geometry of this invention is also characterized by the fact that the aspherical component of the articulation presents a kink (the two circles defining the cross-section of the aspherical component are not tangent) in its contour at the line of contact.

EP0053794, "Cup for a hip joint", by Manfred Semlitsch, et al., discloses an endoprosthesis, in which both the femoral head and the acetabular cup consist of oxide ceramic material, an annular recess is arranged in the area of the opening of the hip joint cup, in which a ring of bioinert, plastically deformable material is situated. The surface of the ring facing towards the joint ball merges, essentially, without interruption and steplessly into the spherical surface of the cup. In the event of subluxation and associated short-term, linear-type bearing contact between joint ball and joint cup at the cup edge, the result, even in the case of dry friction, is a favourable tribology between the joint ball and the ring of plastically deformable material, coming into contact upon subluxation.

EP0821922, "Hip prosthesis joint component with particulate trap", by Claude Hubin and Marie Jean Sterpin, discloses a hip prosthesis cup for metal-metal articulation provided with a polar recess which serves as a trap for wear particles. Alternatively, the head can also have a trap/recess.

FR2727856, "Ensemble prothetique auto-lubrifiant pour l'articulation de la hanche", by Barba Laurent et al., discloses a hard-hard (metal-metal, or ceramic-ceramic) articulation for a total hip prosthesis of such shape and dimensions that a laminar film of synovial fluid can be maintained in use. A reservoir for the fluid is provided at the polar region. No details are provided as to what the geometry of the cup should be to meet the requirement of fluid film lubrication, other than the gap between the cup and the head being in the range of 0.005 and 0.05 mm, which covers the standard radial clearance used in hard-hard bearings.

GB1322680, "Improvement in and related to prosthesis", by Georges Girard and Ramiro Cameo, discloses a total hip prosthesis, whereby the surface of the head is provided by a pattern of grooves intended to reduce the wear at the articulation. As a prior art, the inventors cite a prosthesis whereby the spherical head is articulating against a cup of "football shape", i.e. elongated, which leads to a line contact, rather than a point contact.

US2002/0116068, "Containment system for constraining a prosthetic component", by Terry McLean, discloses a truncated head of a total hip prosthesis which can be inserted into the cup sideways through the slots in the opening of the cup before turning into the functional position. This results in the head being retained within the cup which covers more than 180 degrees. The unintended result is that the conventional point contact is now changed into a line contact along the edge of the truncated segment of the head.

US2005/0246026, "Modular orthopaedic implant apparatus", by Paul Lewis, et al., discloses a modular acetabular cup comprising three elements, which can be combined in different ways to allow the surgeon the choice of implants of varying sizes and features. Fixation is through a central bore of all three, thus, like in U.S. Pat. No. 6,527,809, changing the point contact into line contact along the edge of the liner.

US2005/0261776, "Prosthetic joint with annular contact bearing surface", by Scott Taylor, discloses a truncated, or annular, acetabular component of a total hip prosthesis, whereby the contact of the head and the inner of the two members of the cup occurs along a line instead of at a point.

U.S. Pat. No. 5,181,926, "Bone implant having relatively slidable members", by Rudolf Koch and Robert Streicher, discloses a total hip prosthesis, whereby the cup side, within cavities in its polymeric liner, contains self-aligning pads of hard material which articulate against the head.

U.S. Pat. No. 5,549,693, "Cotyloidal prostheis", by Christiane Roux and Michel Pequignot, discloses a total joint prosthesis, whereby the cup side contains at its opening a ceramic ring, much like a natural labrum, which forms a seal to the ceramic head. Position of the ring is such that the frictional moment of the couple would be very high.

U.S. Pat. No. 5,593,445, "Bi-axial prosthetic joint", by Thomas Waits, discloses a total joint prosthesis whereby a third, ring-shaped, member is interposed between the head and the cup, increasing the contact area under load, self aligning between the head and the cup in the direction of the load.

U.S. Pat. No. 5,702,456, "Implant having reduced generation of wear particulates", by David Pienkowski, discloses a method of pre-wearing the prosthesis before implantation, whereby, the usually somewhat increased, amounts of particles produced by wear-in process do not burden the body. Only minimal improvement of long term outcomes could be expected from such a procedure.

U.S. Pat. No. 5,725,593, "Total anatomic hip prosthesis", by Francesco Caracciolo, discloses a resurfacing total hip prosthesis, whereby the femoral cup has multiple circular rises, intended to reduce the friction within the spherical cup.

U.S. Pat. No. 5,766,258, "Wrist prosthesis", by Beat Simmen, discloses a wrist prosthesis, whereby, in one of the embodiments of the invention, one of the two separate articulations is produced with non-circular members so that they tend to fall, or self-center, into a stable position, in which they become congruent.

U.S. Pat. No. 6,527,809, "Trial acetabulum or implantable acetabulum with adjustable orientation", by Levon Doursounian and Michel Porte, discloses a modular acetabular cup, whereby the cup inlay, which articulates against the head, has a central opening allowing access to the mechanism for locking the cup in the desired position. This, as a side effect, defines the contact conditions between the head and the inlay as a line contact along the edge of the central opening, as is the case in U.S. Pat. No. 4,840,631, "Artificial hip joint socket with hydraulic head support", by Robert Mathys, but without the hydraulic pressure support disclosed by Mathys.

U.S. Pat. No. 4,030,570, "Prosthetic acetabulum", by Otto Frey, discloses a torus-shaped aspherical cup with the radius of the curvature equal to that of the spherical head, but with the center of the curvature offset from the central axis so as to avoid jamming of the head in the cup, changing the theoretical point contact of a sphere in a spherical socket into a line contact of a sphere in a toroidal socket, and further, for the purpose of improved lubrication, a groove at the periphery of the cup and a recess/pocket at the pole. Herzian stresses are reduced, but not eliminated by changing point to line contact, whereas the current invention changes point to surface contact.

U.S. Pat. No. 4,840,631, "Artificial hip joint socket with hydraulic head support", by Robert Mathys, discloses a hip joint articulation with a cylindrical recess machined into the cup creating a reservoir for the joint fluid, which pressurizes under load and seals at the edge of the recess. The disantvantage of this solution is in the high stresses produced at the edge of the recess, which could lead to localized wear, potentially to loss of the seal and hence of hydraulic support.

U.S. Pat. No. 5,336,267, U.S. Pat. No. 5,383,936, U.S. Pat. No. 5,738,686 and U.S. Pat. No. 6,312,471 by Dietmar Kubein-Meesenburg et al. disclose theoretical bases and solutions to reducing stresses in ariculations of joint prosthesis, all of which lead to theoretical line contact instead of point contact. Herzian stresses are reduced, but not eliminated.

GB 1322680, "Prosthesis", by Georges Girard et al. discloses a metal-metal total hip joint articulation, whereby the concave, cup, component is provided with multiple grooves, leaving only protrusions, ending on a spherical surface, to contact the spherical head. This type of contact is proposed to reduce the risk of jamming in conventional, smooth, spherical surfaces of the ball-in-socket joint, specifically in metal-metal combination, where the required tolerances are tight and difficult to maintain in production.

U.S. Pat. No. 6,645,251, "Surfaces and processes for wear reducing in orthopaedic implants", by Abraham Salehi et al. discloses an approach based on grooving the concave surface in order to improve lubrication and distribute the stress. As known from technical sliding bearings, the main advantage of grooves comes from improved removal of wear particles away from the articulation. Fluid entrapment may play a role in improved lubrication as well. However, grooves as disclosed may in fact lead to higher local stresses at the edges of the grooves and defeat the purpose. There has been no published data supporting the concept and no evidence of even limited acceptence of this approach by the orthopaedic device industry.

U.S. Pat. No. 6,425,921, "Sliding partners for artificial joint implants", by Hans Grundei and Wolfram Thomas, discloses an alternative approach where the grooves are produced in the convex component of the joint. Actual hip simulator tests performed on this type of joint components did not show any wear reduction.

U.S. Pat. No. 6,800,095, "Diamond-surfaced femoral head for use in a prosthetic joint", by Bill J. Pope et al., discloses a super-hard bearing surface produced by diamonds attached to a metalic substrate of the femoral head.

U.S. Pat. No. 6,488,715, "Diamond-surfaced cup for use in a prosthetic joint", by Bill J. Pope et al., discloses a super-hard bearing surface produced by diamonds attached to a metalic substrate of the acetabular cup.

U.S. Pat. No. 4.846,841, "Femoral prosthesis", by Indong Oh, discloses a femoral prosthesis, which connects the prosthetic head to the remnant of the femoral head and neck by a shell covering the reamed bone with internal features which allow for bony integration without bone cement.

U.S. Pat. No. 5,258,033, "Total hip replacement femoral component", by Peter Lawes and Robin S.M. Ling, discloses a femoral resurfacing component intended for cemented fixation, whereby the inner surface of the prosthetic head is tapered so as to lead to compression of the cement mantle if the interface between the cement and the head gets loose.

U.S. Pat. No. 6,626,949, "Diamond coated joint implant", by Charles 0. Townley, discloses a joint prosthesis, wherein one or both articulating surfaces are made from a polymer and is/are coated by diamond to reduce wear.

U.S. Pat. No. 6,090,145, "Partial scaphoid implant and method of treating ailments of the scaphoid", by Michal Hassler and Jean-Pierre Pequignot, discloses a partial prosthesis of scaphoid made from pyrolytic carbon.

Partial and total finger, hand and wrist joint prostheses, as well as a radial head prosthesis produced from pyrolytic carbon and graphite have been in clinical use for over 20 years and are commercially available from e.g. Tornier, Saint-Ismier codex, France and from Ascension Orthopedics, Inc., Austin, Tex., USA.

WO/2005/094731, "Double shell implant for cementless anchorage of joint prostheses", by Slobodan Tepic and Henrik Malchau, discloses a compliant, hydraulically open, double shell construct for metal backing of joint prostheses with a perforated shell for rapid bony integration.

US 2006/0178737, "Coated medical apparatus", by Leo T, Furcht, discloses use of diamond coating on any portion of the surface of the medical apparatus. The inventor is clearly not informed about the state-of-art—various diamond coated implants have long been in clinical use.

U.S. Pat. No. 4,129,903, "Hinge prosthetic joint with ball head", by Arnold H. Huggler, discloses a method of fixation of a prosthesis, including an endoprosthesis of the hip, by means of a tension device which maintains a force on a pressure disc placed over the neck osteotomy.

U.S. Pat. No. 5,549,704, "Universal joint prosthesis", by Franz Sutter, discloses a method of fixation of a femoral head resurfacing prosthesis, using perforated cylinders to anchor the prosthesis into the cancellous bone of the femoral head and neck.

U.S. Pat. No. 6,197,065, "Method and apparatus for segmental bone replacement", By Daniel L. Martin and John Robert White, discloses a method of implant fixation on a transversally cut bone, by means of a compliant tension anchor which maintains load on the implant-bone interface, providing stability for bony ingrowth, even if an incidental load causes a brief disruption in the process of integration.

Practical limitations to the accuracy of the machinable components, including effects of temperature and of radiation-induced shrinkage, if used for sterilizing polymeric cups, and the protection against the jamming of the components when used in the body, have led to international standards which guarantee acceptable in vivo performance.

ISO standards 7206-2; 27.80 to 28.00 and 7206-2; 28.10 to 28.30 specify the geometry and dimensions of the head and cup components, respectively, of a total hip prosthesis.

Sphericity and dimensional tolerance of the head component—The metal or ceramic femoral head component of a total hip prosthesis shall have a departure from roundness of not greater than 10 micrometers. If used against hard material cups (metallic or ceramic), it will not be greater than 5 micrometers. The diameter shall be equal to nominal diameter +0.0, −0.2 mm. For metal-metal or ceramic-ceramic articulations. the tolerances are not specified, but in all cases there shall be radial clearance. In practice, the heads are today produced with significantly tighter specifications than required by the standards.

Sphericity and dimensional tolerance of the cup component—For a polymeric component the sphericity is not specified; for hard materials it shall not exceed 5 micrometers. The dimensional tolerance for a polymeric cup is +0.3, +0.1 mm at 20±2 deg C. from the nominal diameter. In practice, UHMWPE cups are oversized by at least +0.2 mm over the nominal diameter. No tolerances for the metallic or ceramic cups are given, but the radial clearance must be guaranteed by the producer. Typical radial clearance for hard pairs is in the range of 0.02 to 0.030 mm.

Partial hip prostheses, such as Austin-Moore, were the first to be clinically used, fairly commonly, since the fifties. The femoral head, produced from either a metallic or ceramic material, is highly polished and intended to articulate against the natural cartilage of the acetabulum. A dominant current type is the, so-called, bi-polar partial hip prosthesis, wherein the standard femoral component, usually cemented, is complemented by a second, large head, placed over the standard smaller one, and is matched to the size of the acetabular cavity. In contrast to the Austin-Moore prosthesis, bi-polar designs are modular and allow for more flexibility in neck length sizing.

Functional limitations of partial prosthesis are largely related to a relatively short life of the acetabular cartilage, which, when worn out, leads to a painful joint due to poor frictional properties of the metal-on-bone or ceramic-on-bone articulation. Bi-polar designs aim at solving the problem by providing a secondary articulation between the large head, fitted into the acetabulum, and the small head, attached to the stem. However, there are problems with the proposed mechanism. The frictional moment between the large head and the cartilage is lower than the frictional moment between the large and the small head, as long as the cartilage is functional, so most of the movement occurs within the acetabulum. Once cartilage is damaged, movement will shift to the inner articulation, but the large head, with its poor frictional properties, will still occasionally move and wobble within the bony bed. This leads to surface damage of the relatively soft outer head and accelerates wear at the bone to outer head articulation. All along, the position of the outer head on the inner one is not ideal, leading to both impingement of the outer head on the neck of the stem and loss of the articulating surface within the acetabulum.

U.S. Pat. No. 3,510,883, "Joint prosthesis", by R. F. Cathcart Ill, discloses a modified Austin-Moore type partial hip joint prosthesis, wherein the head of the prosthesis is a-spherical in order to cause pumping action on the acetabular cartilage. The oval shape of the Cathcart prosthesis is intentionally used to reduce congruency to the spherical cavity of the acetabulum, hence advocating a principle diametrically opposed to that of the present invention. In an appendix of his Masters Thesis, "Congruency of the human hip joint", Massachusetts Institute of Technology, Cambridge, 1980, Tepic provides a computer simulation of the measurements performed by Cathcart on human femoral heads, illustrating how his method deficits could have led him to his erroneous conclusions on the shape of the natural femoral head, which, in fact, is extremely spherical.

In his doctoral thesis, "Dynamics of and entropy production in the cartilage layers of the synovial joint", Massachusetts Institute of Technology, Cambridge, 1982, Tepic provides experimental and analytical background for this invention, which is a crude emulation of the natural synovial joint in that: (1) low frictional losses are due to synovial fluid "weeping" (a cartilage lubrication mechanism proposed by McCutchen; see Lewis P R, McCutchen C W, "Experimental evidence for weeping lubrication in mammalian joints", Nature, 1959 October 24; 184:1285) out from a reservoir sealed by the contact of the two joint components, and that (2) the solid contact at the seal around the reservoir is itself low friction, in the case of the artificial femoral head, due to the diamond-like coating.

Partial hip prosthesis manufactured from different materials were tested in dogs with intact articular cartilage (see, Cook S D, Thomas K A Kester M A, "Wear. Characteristics of the Canine Acetabulum Against Different Femoral Prostheses," JBJS, 1989; 71-B(2): 189-197). Probability of cartilage survival at 18 months against pyrolitic carbon femoral head was 92%; with cobalt-chromium and titanium alloys probability was only 20%.

In vitro wear testing of cortical bovine bone articulated against spherical implants manufactured from zirconia, cobalt-chromium, titanium and pyrolitic carbon (see, Strzepa P, Kiawitter J, "Ascension PyroCarbon Hemisphere Wear Testing Against Bone," Poster No. 0897, 51st Annual Meeting of the Orthopedic Research Society) showed significant, two orders of magnitude lower wear with pyrolitic carbon than with any other material. Coefficient of friction of pyrolitic carbon and ADLC treated metals against most hard materials, including bone, is approximately 0.05—at least an so order of magnitude lower than bone on bone, or any other known hard material on bone.

SUMMARY OF THE INVENTION

The invention reduces friction and wear in partial hip prosthesis by combining optimized geometry of the articulation and surface treatment of the prosthetic component. The acetabulum is reamed to the bone. One of the articulating surfaces—either that of the reamed acetabulum, or that of the femoral head prosthesis is a-spherical so that a fluid-filled gap is formed at the area of major load transfer. The fluid-filled gap is sealed by an annular area of contact, over which the concave and the convex components are congruent. The preferred surface treatment is by diamond-like coating, which results in very low coefficient of friction and high abrasion resistance against the bone. The prosthetic head is fixed to the femur by either a conventional stem, by a perforated shell, or by a femoral neck prosthesis screwed onto the femur so that it is partially covered by bone and partially exposed on the medial-inferior aspect, where it abuts the reamed cortex of the calcar region.

According to one aspect of the invention, a partial hip prosthesis is provided wherein one and only one of the articulation members is spherical in shape allowing for free rotation of the other articulation member, which is aspherical in shape and is shaped so as to make an annular, congruent contact to the spherical member. An artificial joint articulation may include a head articulated within a bony cavity formed by reaming of the acetabulum.

The bony cavity may be spherical in shape and the head may be flattened at the area of major load transfer, leaving a fluid-filled gap to provide for improved lubrication. Alternatively, the bony cavity may be aspherical—deepened at the area of major load transfer—and the head may be spherical, resulting again in a fluid-filled gap to provide for improved lubrication.

The geometry of the head and the reamed cavity may be such as to form a desired contact surface. The contact surface may include a circular area of substantially spherical shape about an axis of revolution, the axis of revolution being oriented along the major joint force vector.

The head is preferably produced from a biocompatible metal, e.g. a titanium alloy, a cobalt-chromium alloy, or a stainless steel alloy and may be coated by a hard, low friction coating such as amorphous diamond-like coating (ADLC). Alternatively, the head may be produced from carbon, e.g. a pyrolytic carbon, with essentially the same surface characteristics as ADLC.

The prosthetic head may be affixed to the femur by means of a perforated shell suitable for rapid bony integration.

According to yet another aspect of the invention, a partial hip prosthesis is provided wherein the prosthetic head of the femur is affixed to the neck of the femur via a cylindrical prosthetic neck abutting the reamed femoral neck from outside the medial-inferior cortex, while crossing the anterior and the posterior cortices of the femoral neck to engage the lateral-superior area of the femoral neck from within. The prosthetic head may be affixed to the femur by means of a unique, novel neck prosthesis, which is screwed onto the resected head and neck portion of the femur, so that the medial-inferior aspect of the prosthetic neck is located outside the medial-inferior aspect of the femoral neck and is abutted to the cortical bone in the calcar zone, while in the lateral-superior aspect the prosthetic neck engages the bone from inside. The prosthetic neck leaves a substantial mass of the cancellous bone of the proximal femur intact, yet provides a very stable load transfer to the calcar cortex. The prosthetic neck can be perforated for rapid bony integration and improved vascular supply of the new and remodeled bone.

The femoral head prosthesis can be affixed to the femur by a conventional stem, should the condition of the bone in the head-neck region be such that neither of the first two means could be used.

The surface of the head may be highly polished prior to coating, to minimize wear of the bone and reduce friction-induced heat production to below the threshold of thermal necrosis.

The prosthetic component facing the bone may be treated for optimal bony integration, including e.g. porous coatings and porous surfaces produced by chemical-physical etching, optionally treated to include minerals similar to those of bone tissue.

According to another aspect of the invention a method is provided of surgical treatment of the hip joint with a partial hip prosthesis, wherein one and only one of the articulation members is spherical in shape allowing for free rotation of the other articulation member, which is aspherical in shape and is shaped so as to make an annular, congruent contact to the spherical member.

According to yet another aspect of the invention, an aspherical acetabulum reamer is shaped so as to ream the bone with a spherical band, a recess at the polar region and an equatorial region wider than the diameter of the sphere corresponding to the spherical band.

The skilled person may recognize that the above-indicated aspects of the invention may be combined with each other.

DETAILED DISCLOSURE

For a simple and clear presentation, a human total hip joint articulation has been chosen for this disclosure, but the same technical arguments and design approaches can be used for a hip prosthesis for animals, specifically for dogs and cats.

The present invention is an extension of a prior invention by the inventor as set forth in PCT Patent Application No. WO2008/058756, published on May 22, 2008, which is incorporated herein, in its entirety, by reference ("the Tepic Application"). The Tepic Application discloses a joint prosthesis, such as a hip prosthesis, in which the convex and concave components have differences in shape to provide a broad contact surface. As set forth in the Tepic Application, the differences in shape between the components further provide improved lubrication of the components and particularly the contact surface. While that structure results in significantly reduced wear, it may still be of a concern, particularly when the concave component is formed of UHMWPE. The wear can be further reduced by the so present invention, in which the head is treated by ADLC and, most importantly, reduced to wear of only the biological materials present in bone, which are readily re-absorbed by natural mechanisms.

Major reduction in production and clinical application costs are expected in partial hip replacement according to the invention. Surgical time can be reduced by about 15 minutes. Post surgical complications will also be less likely, particularly dislocation of the hip and incidence of lung embolism. The procedure is well suited to so-called minimally invasive approaches to the hip joint. Of the traditional approaches, both the anterior-lateral and the posterior approach can be used, i.e. no new surgical skills are necessary. Should a revision be indicated, it would be a simple matter to convert a partial prosthesis according to this invention to a conventional total hip replacement.

Figure 1:
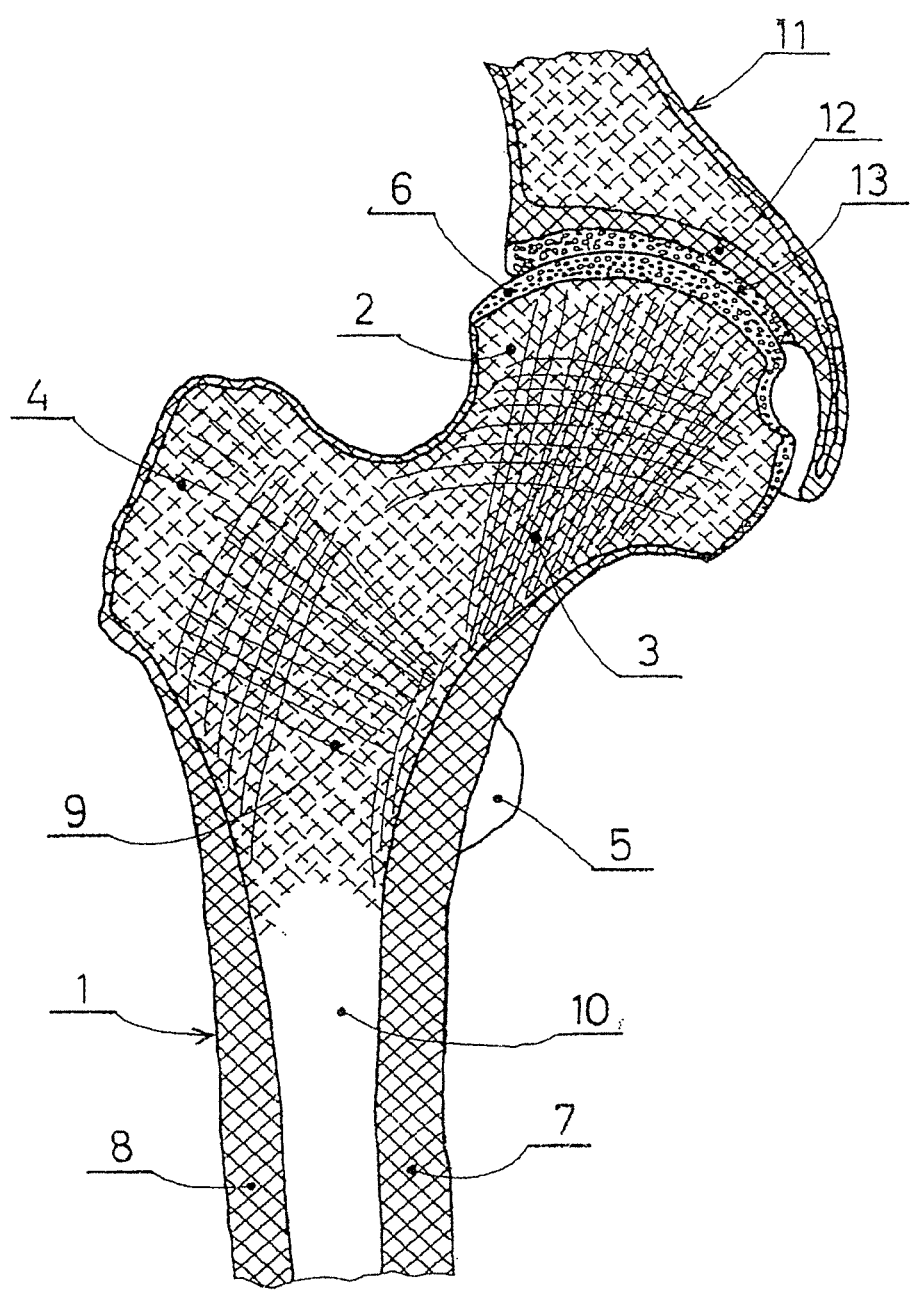
FIG. 1 is a schematic cross sectional view of the hip joint.

FIG. 1 shows a schematic cross sectional view of the human hip joint. The femur 1 on its proximal medial aspect comprises the femoral head 2 and the femoral neck 3. The greater trochanter 4 anchors most of the tendons of the muscles pulling towards the pelvis, e.g. piriformis, gluteus minimus, gluteus medius, quadratus femoris, obturator externus and internus, but also and in continuity, of the tendons of the muscles acting in the distal direction towards the knee joint, particularly of vastus lateralis. The lesser trochanter 5 anchors the tendons of psoas major and iliacus. The femoral head is covered by cartilage 6. The medullary cavity 10 of the shaft of the femur in the cross sectional view is defined by the medial cortex 7 and the lateral cortex 8. It is filled by fatty marrow, which poses a high risk of lung embolism if extruded into circulation via distal venous drainage by pressurization of the cavity during preparation for and/or insertion of a classical stemmed femoral component. Proximal aspect 9 of the femur is filled by cancellous bone. The pelvis 11 receives the head in its concave acetabulum, defined by the subchondral bone 12, covered by cartilage 13.

Figure 2:
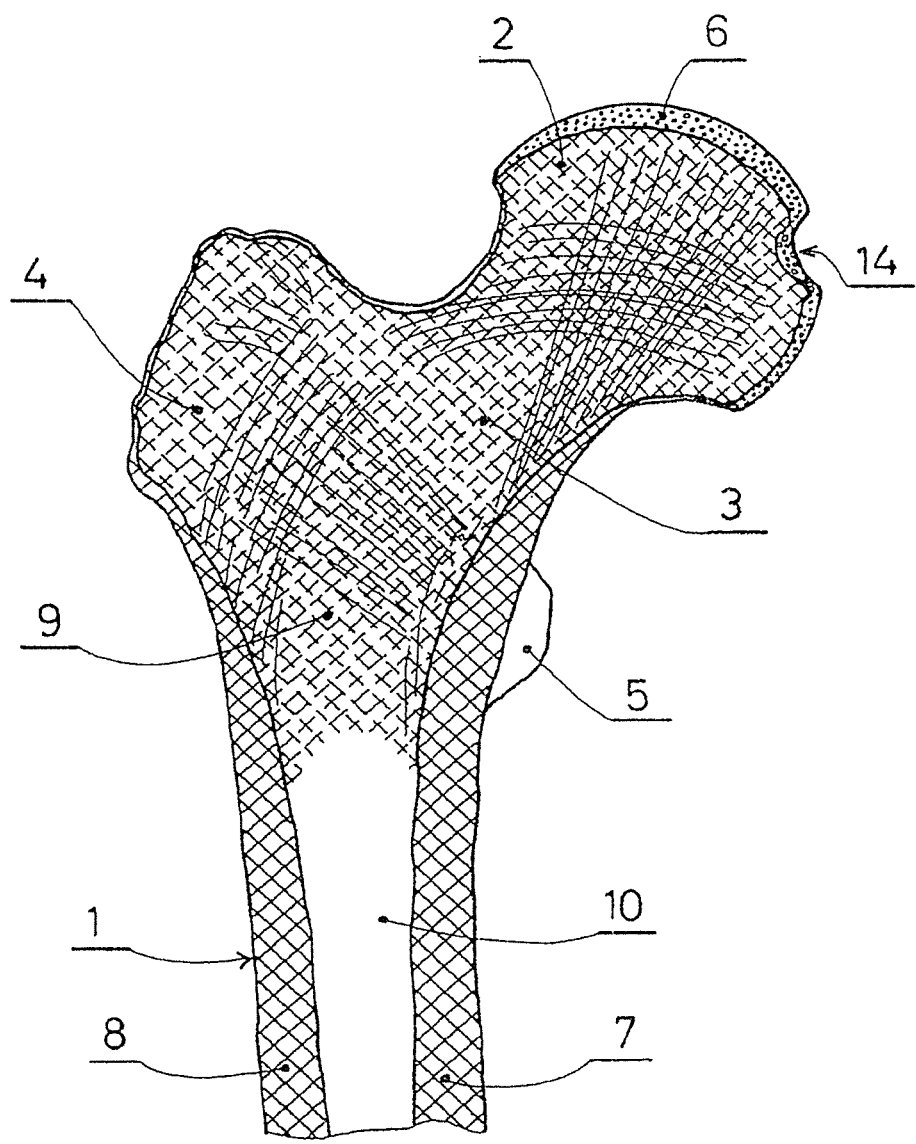
FIG. 2 is a schematic cross sectional view of the proximal femur.

FIG. 2 shows a schematic cross sectional view of the proximal femur alone. The head 2 is covered by cartilage 6 over little more than a hemisphere facing superiorly, medially and slightly anteriorly. Fovea 14 of the femoral head receives the ligament of the head of the femur.

Figure 3:
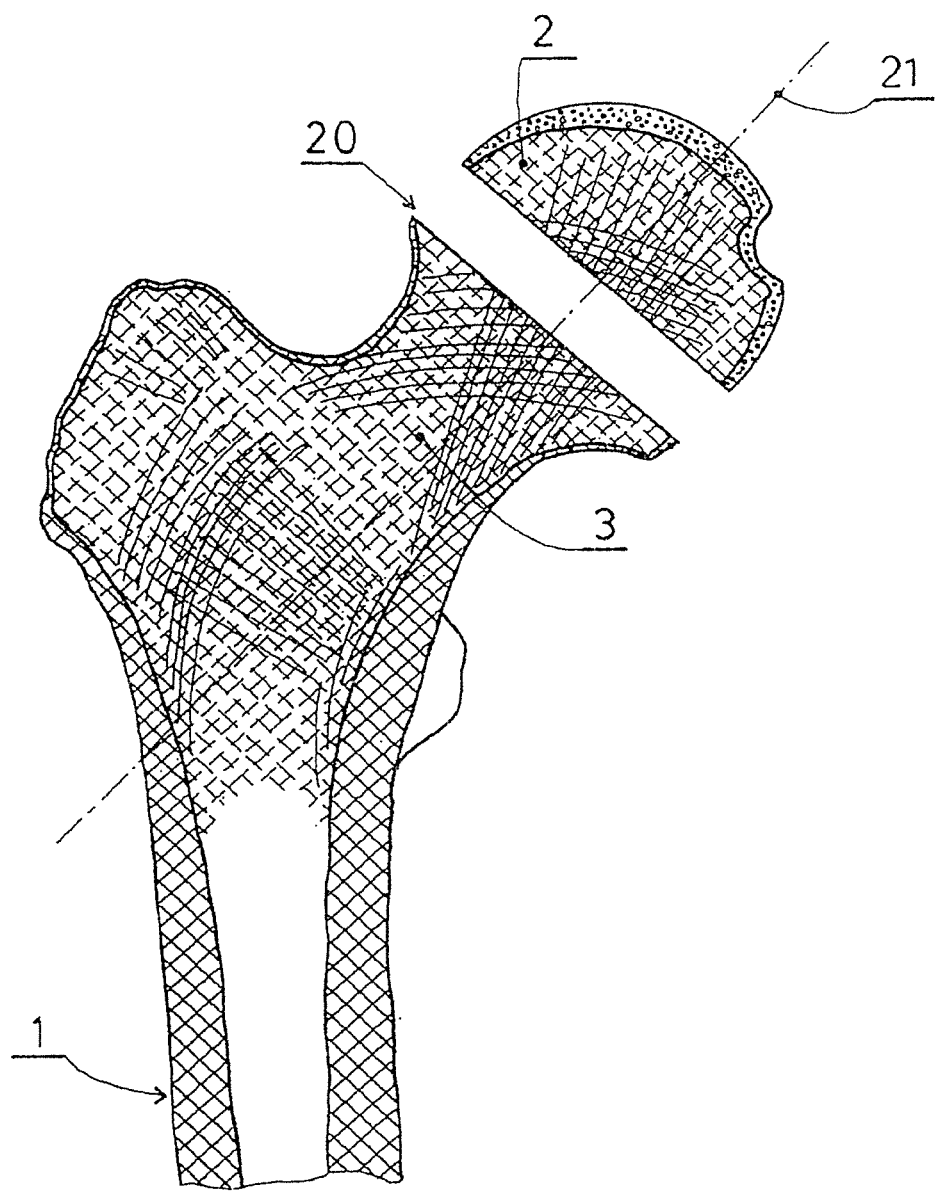
FIG. 3 is a schematic cross sectional view of the proximal femur with the femoral head partially resected.

FIG. 3 shows the first step of the surgical procedure required to attach the prosthesis to the femur—the head 2 is resected from the neck 3 by a saw cut along the plane 20, approximately along its "equator" and at approximately 90 degrees to the axis 21 of the neck 3 of the femur.

Figure 4:
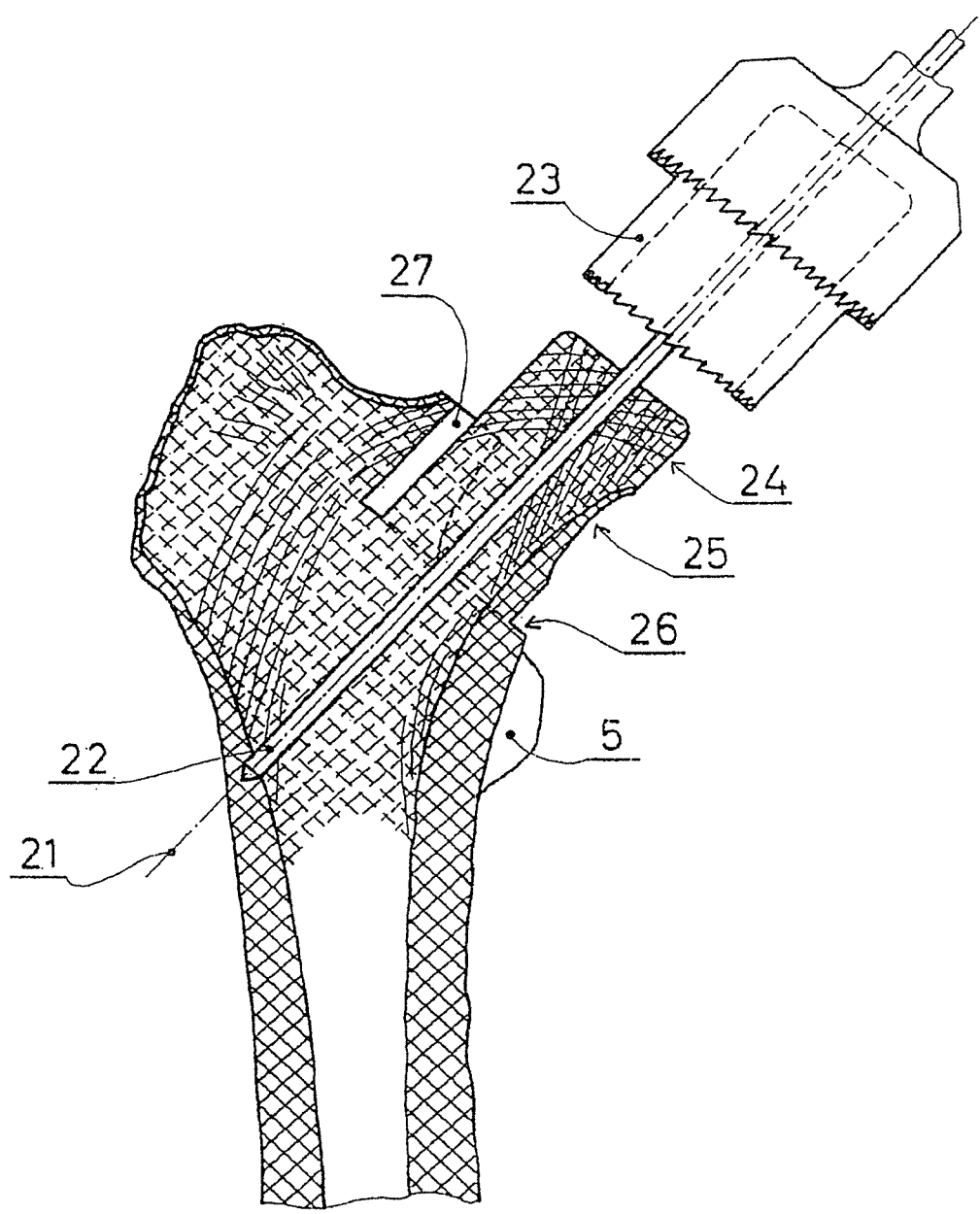
FIG. 4 is a schematic cross sectional view of the proximal femur with the femoral head partially resected and the femoral neck reamed over a guide pin.

FIG. 4 shows the next step of surgical femur preparation. A guide pin 22 is inserted along the neck axis 21 and a cannulated cylindrical reamer 23 is used to cut a cylindrical groove 27 centered onto the pin 22. With the proper placement of the guide pin 22 and the proper size of the reamer 23, the neck of the femur will end up having a proximal, fully reamed portion 24, a partially intact medial-inferior cortex 25 and a distal abutment 26 in the calcar region of the femur, just above the lesser trochanter 5.

Figure 5A:
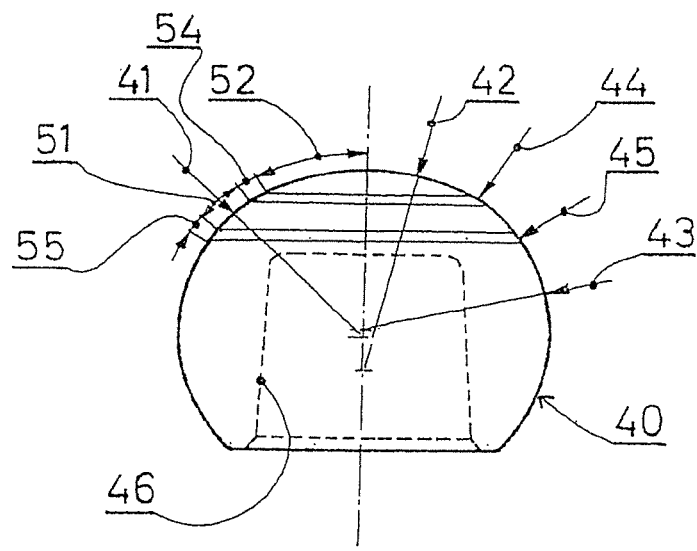
FIGS. 5a-5b are perspective views of the femoral head prosthesis and the femoral neck prosthesis according to the invention.

FIG. 5a shows a perspective view of the prosthesis head 40. The section of the head along the band 51 has a radius of curvature 41, equal to the radius of the spherically reamed acetabulum. The polar region of the head denoted by 52, has a radius of curvature 42, which is larger than 41. The lower section of the head has the radius of curvature 43, which is smaller than 41. For production convenience the three sections (with radii 41, 42 and 43) can all be spherical in shape and their centers can lie on the main axis of the head. The transition band 54 between the sections 51 and 52 has a small radius of curvature 44. The transition band 55 between the section 51 and the lower section of the head, has a radius 45. With these transitions the finished head has a smooth, axisymmetric outer contour. Inside, the head is provided with a conical recess 46. Several lengths of the head can be provided, as usual in the hip systems, by machining the conical recess deeper or shallower into the head.

A complete system for treating patients with the partial hip prosthesis according to the invention would have base diameter of the head (2 times the radius 41) in the range from about 40 to about 70 mm, in increments of either 1 or 2 mm. The angle defining the position of the middle of the band 51, measured from the axis of the head should be in the range from about 30 to about 55 degrees, the theoretical best being at 45 degrees. The width of the band 51 should be from about 5 to about 15 degrees. The radius 42 at the polar zone can be several millimeters larger than the radius 41, e.g. 2 to 4 mm, while the radius 43 should be smaller by about 0.2 to 1 mm.

Figure 5B:
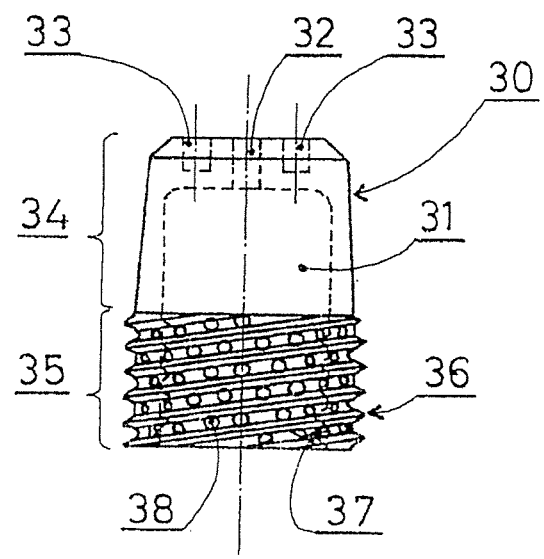

FIG. 5b shows a perspective view of the prosthesis neck 30. The upper part 34 of the neck prosthesis is conical in shape, 31, adapted to fit into the conical recess 46 of the head 40. A central hole 32 allows for insertion into/onto the reamed neck of the femur over the guide pin 22. Recesses 33 provide means for engaging the implant with an instrument to screw it into/onto the neck of the femur. The lower part 35 of the neck prosthesis engages the bone by both outer threads 36 and inner threads 37 of the same pitch. A number of optional holes 38 preferably placed between the threads are intended for better vascular supply of the new bone which will form around the implant.

Figure 6:
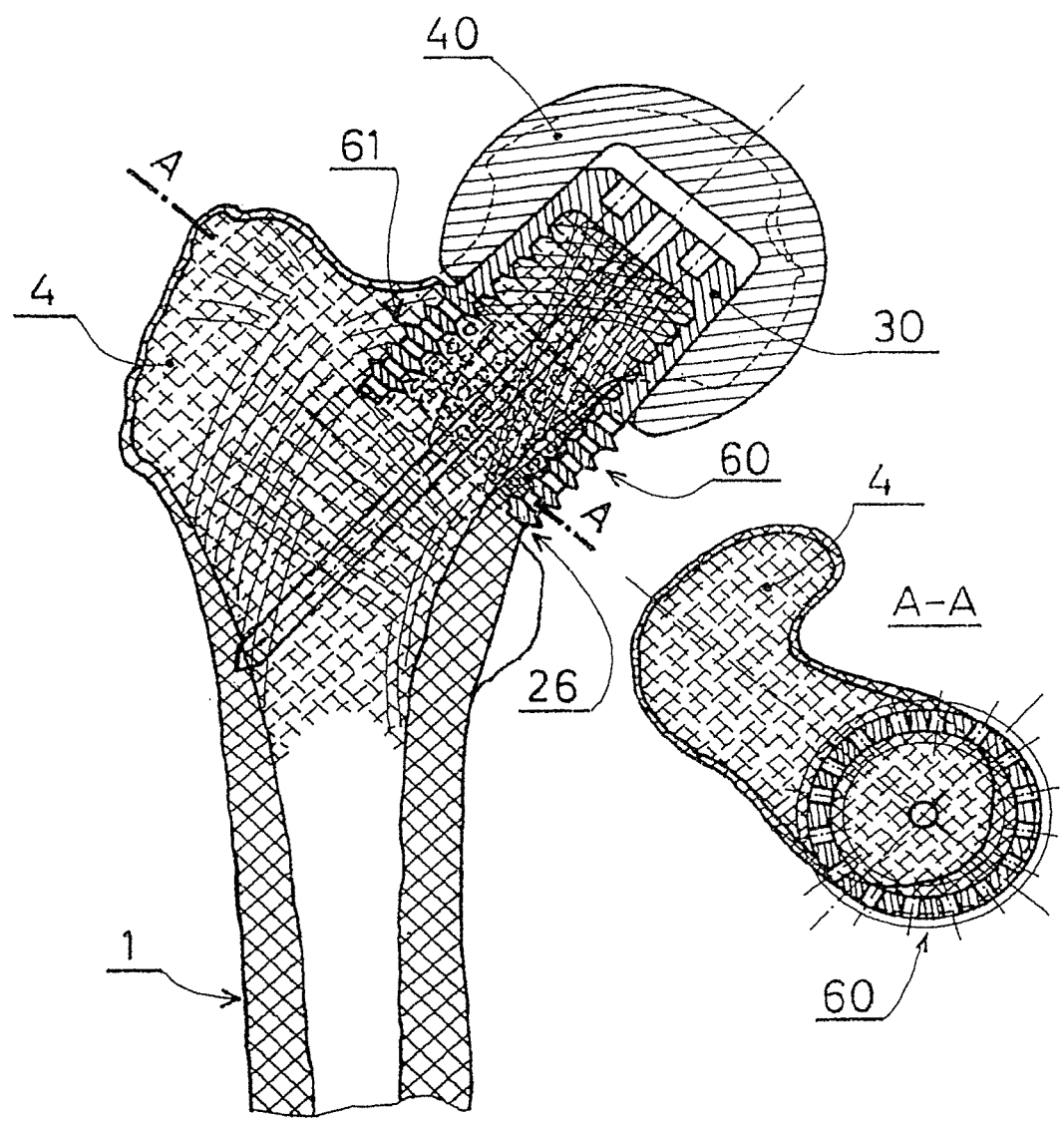
FIG. 6 is a schematic cross sectional view of the proximal femur with the femoral head prosthesis and the femoral neck prosthesis affixed to the femur.

FIG. 6 shows a cross sectional view of the proximal femur 1 implanted with a prosthesis according to the invention. The prosthesis comprises the head 40 and the neck 30. On the medial-inferior aspect 60, the prosthetic neck skims over the outside of the natural femoral neck, engaging it with its inner threads, and abuts the cortex at the reamed abutment 26. On the lateral-superior aspect 61, the prosthetic neck engages the bone of the resected and reamed natural neck by both inside and outside threads. The cross section along the plane A-A shows how the prosthetic neck transsects the natural neck at its anterior and posterior cortices so that at the aspect 60 of the prosthetic neck is outside the natural neck.

This is a unique, novel and fundamentally important feature of the prosthesis neck according to the invention. It allows for load transfer to the strong bone of the medial cortex at the abutment 26, while providing stability against tilting medially over the abutment by anchorage to the lateral aspect of the natural neck and by transecting the cortices of the neck. The cancellous bone of the neck remains relatively intact, disturbed by only the guide pin.

Figure 7:
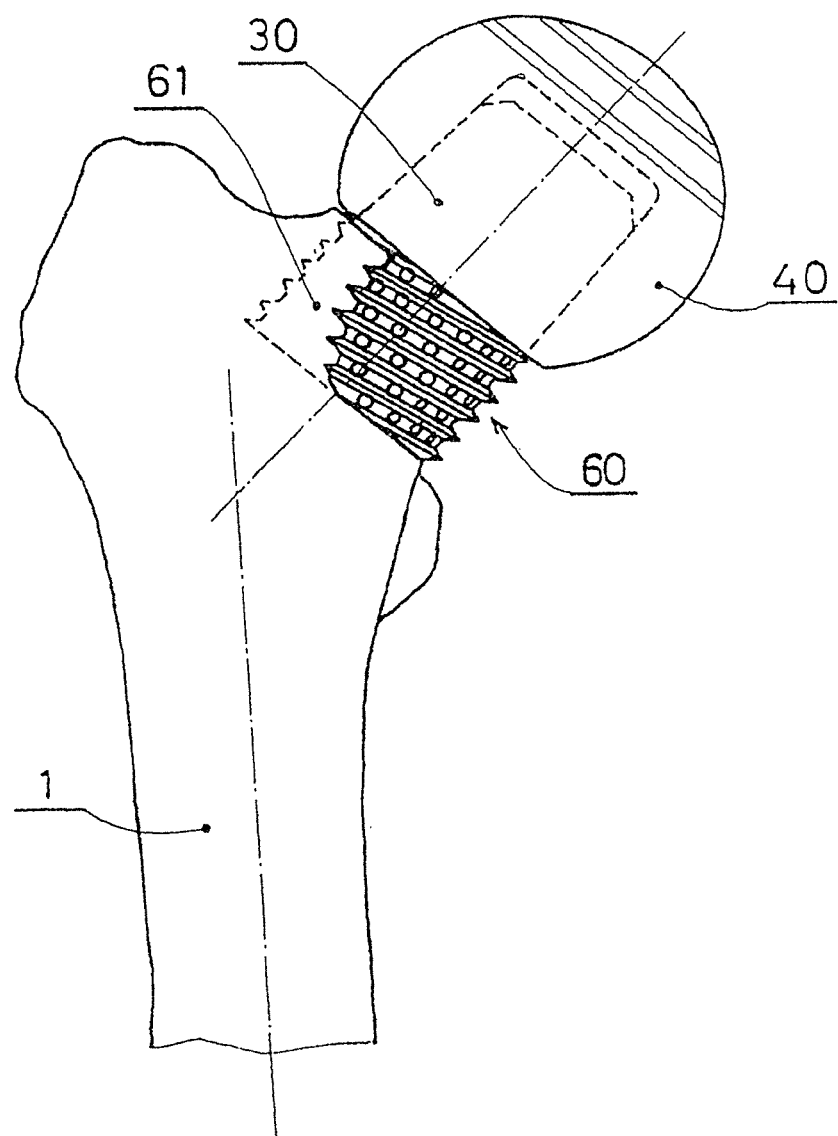
FIG. 7 is a schematic perspective view of the proximal femur with the femoral head prosthesis and the femoral neck prosthesis affixed to the femur.

FIG. 7 shows a perspective view of the anterior aspect of the proximal femur 1 implanted with a prosthetic neck 30 and a prosthetic head 40. The neck 30 is visible on the medial-inferior aspect 60 and hidden by bone on the lateral-superior aspect 61.

Figure 8:
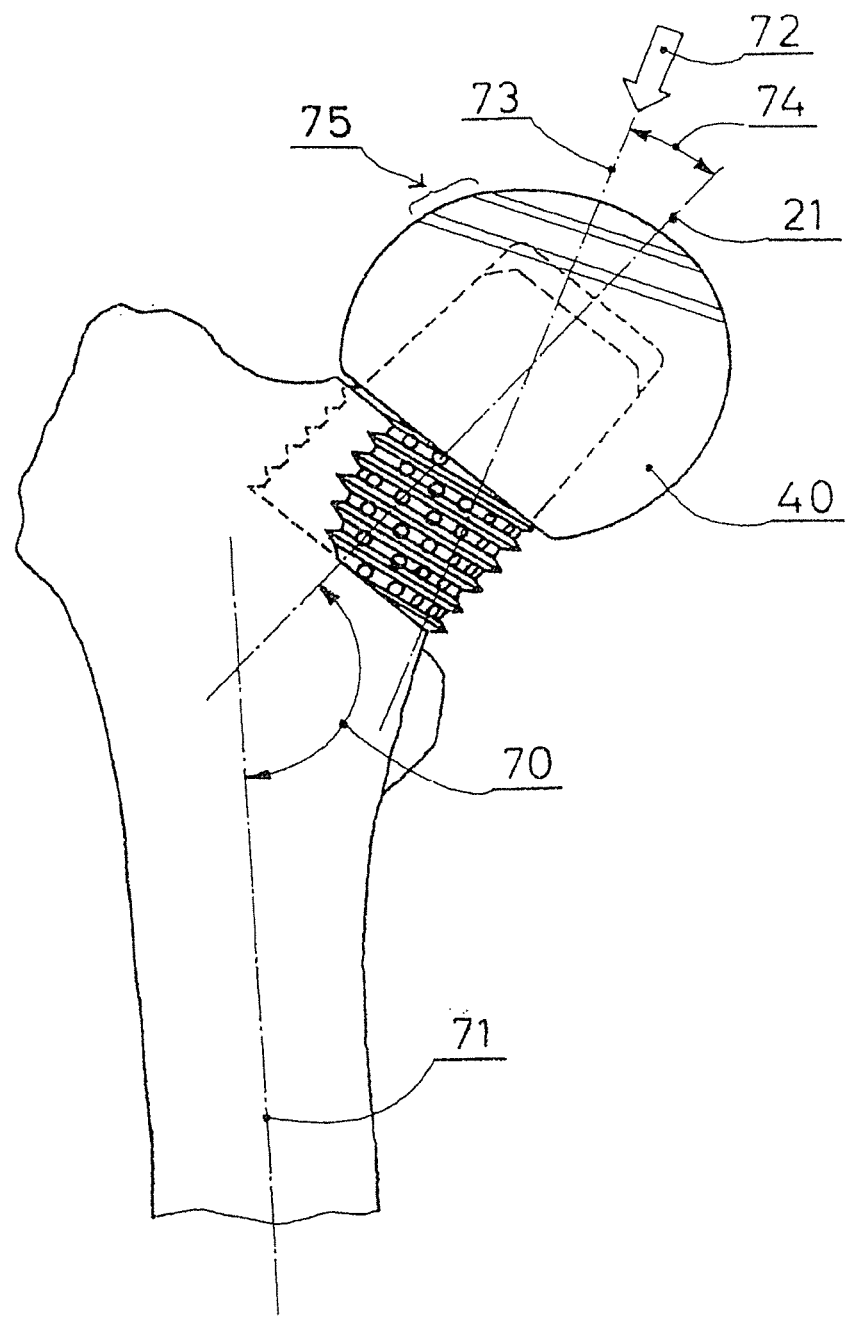
FIG. 8 is a schematic perspective view of the proximal femur with the femoral head prosthesis and the femoral neck prosthesis affixed to the femur, wherein the flattened head feature of the prosthetic head is offset from the neck axis to line up along the major joint force vector.

FIG. 8 shows a perspective view of the anterior aspect of the proximal femur implanted with a prosthetic neck 30 and a prosthetic head 40. The aspherical feature of the head is now centered on axis 73, offset from the axis of the neck 21 by an angle 74. The angle 70 between the femur shaft axis 71 and the femur neck axis 21 is typically about 135 degrees, but it shows significant patient-to-patient variation. The purpose of the offset angle 74 is to bring the flattened section of the head surrounded by the annular section 75, which closely fits the spherical cavity of the acetabulum and thus seals the pool of fluid trapped between the head and the acetabulum, in closer alignment to the joint load 72. Direction of the load 72 does change with activities of the patient, but with an offset of about 15 to 35 degrees, preferably about 25 degrees, the chances are good that the pool will remain sealed for the majority of the angles and forces across the hip joint. The angle 74 should not be in the frontal plane, but rather within a pine with about 15 degrees of antiversion. For the surgeon to place the head into an optimal position the head needs a marking, best on the bottom of it facing the bone once attached to the neck, for the intended placement with the flattened feature facing anteriorly, medially and superiorly.

Figure 9:
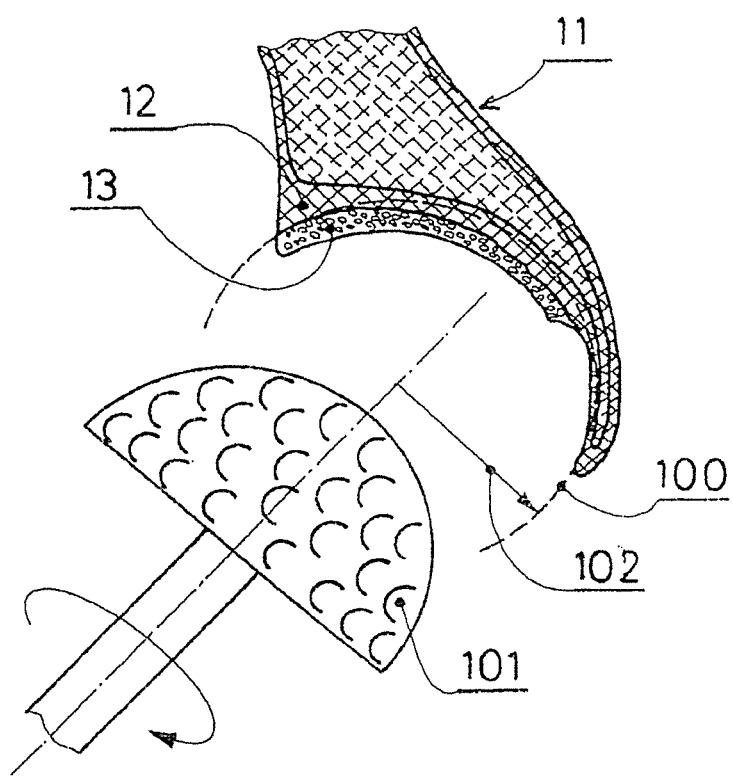
FIG. 9 is schematic partial cross sectional view of the acetabulum reamed-out to bone to create a spherical cavity for the head.

FIG. 9 shows the surgical preparation of the acetabulum in the pelvic bone 11 with a spherical reamer 101. The layer of cartilage 13, usually severely damaged by arthosis of the joint, and some of the subchondral bone 12 are reamed out to a spherical shape 100 with a radius 102. As mentioned earlier, the radius 102 should be equal to the radius 41 of the head, FIG. 5.

Figure 10:
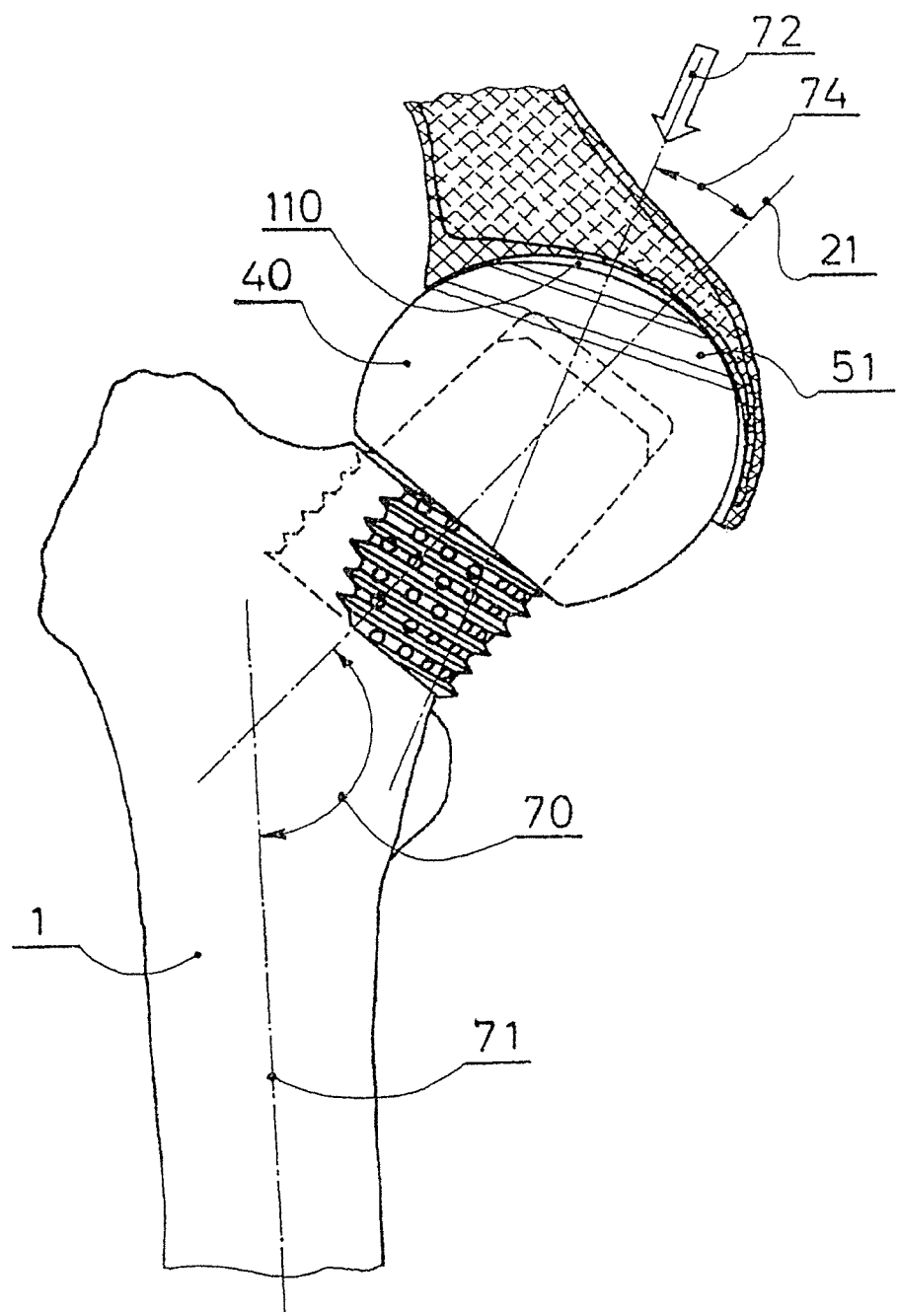
FIG. 10 is a schematic partial cross sectional view of the hip prosthesis according to the invention articulated within a spherically reamed acetabulum.

FIG. 10 shows a perspective view of the anterior aspect of the proximal femur 1 implanted with a prosthetic head 40, placed within the reamed acetabulum, which is shown in a schematic cross sectional view. Between the head 40 and the reamed bone, there is a gap 110, which holds lubricating synovial fluid, sealed therein by the band of contact, which the matching section 51 of the head 40 makes with the reamed acetabulum. The major joint load 72 is offset from the neck axis 21 by the angle 74.

Figure 11:
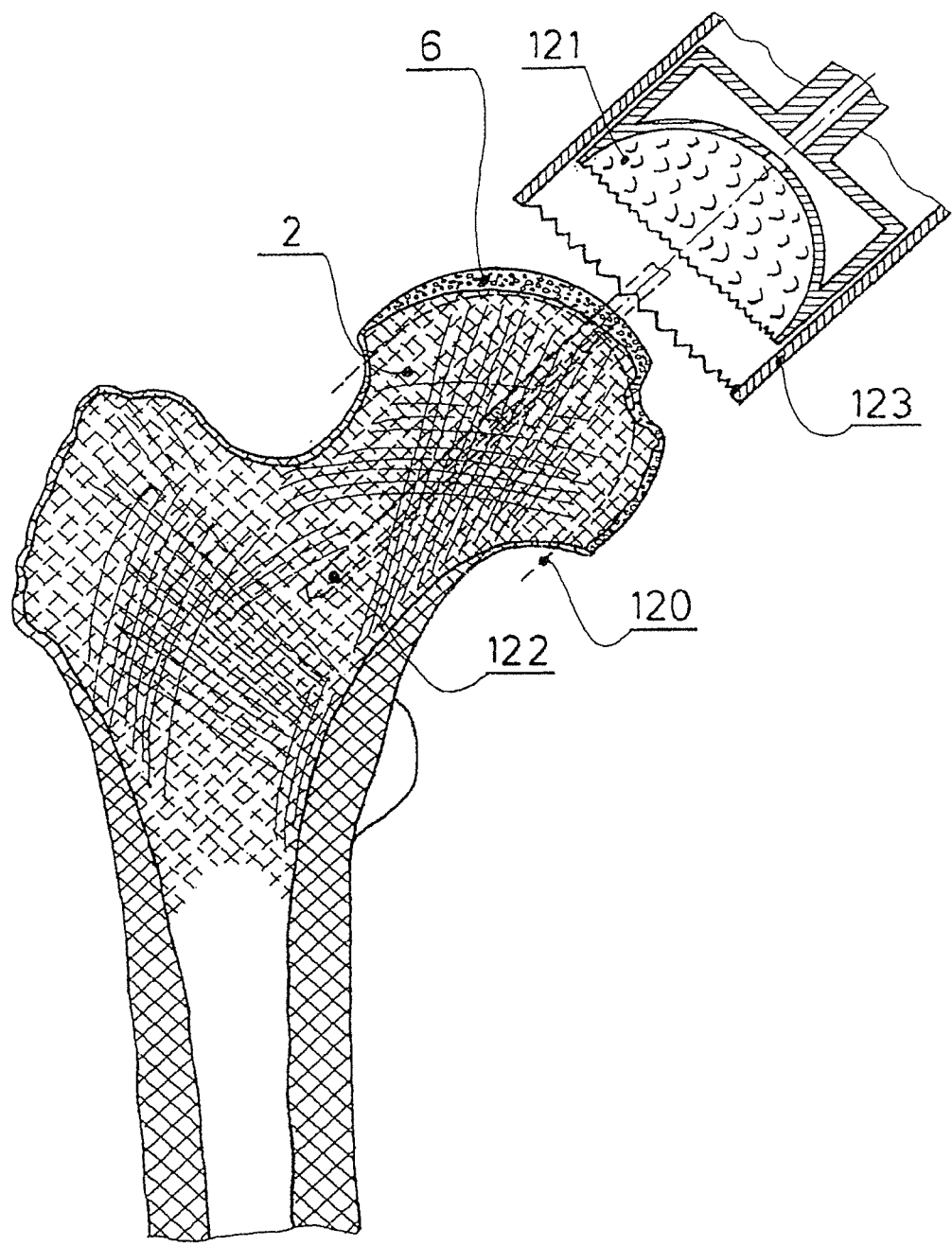
FIG. 11 is a schematic cross sectional view of the femoral head spherically reamed to remove the surface layer of damaged cartilage and bone.

FIG. 11 shows an alternative surgical preparation of the head of the femur. The layer of cartilage 6 is reamed together with some supporting cancellous bone to the spherical-cylindrical shape 120, by the reamer 121. The reaming is performed over a guide pin 122; the serrated sleeve 123 can also be used to guide the reamer 121 centered on the head 2.

Figure 12:
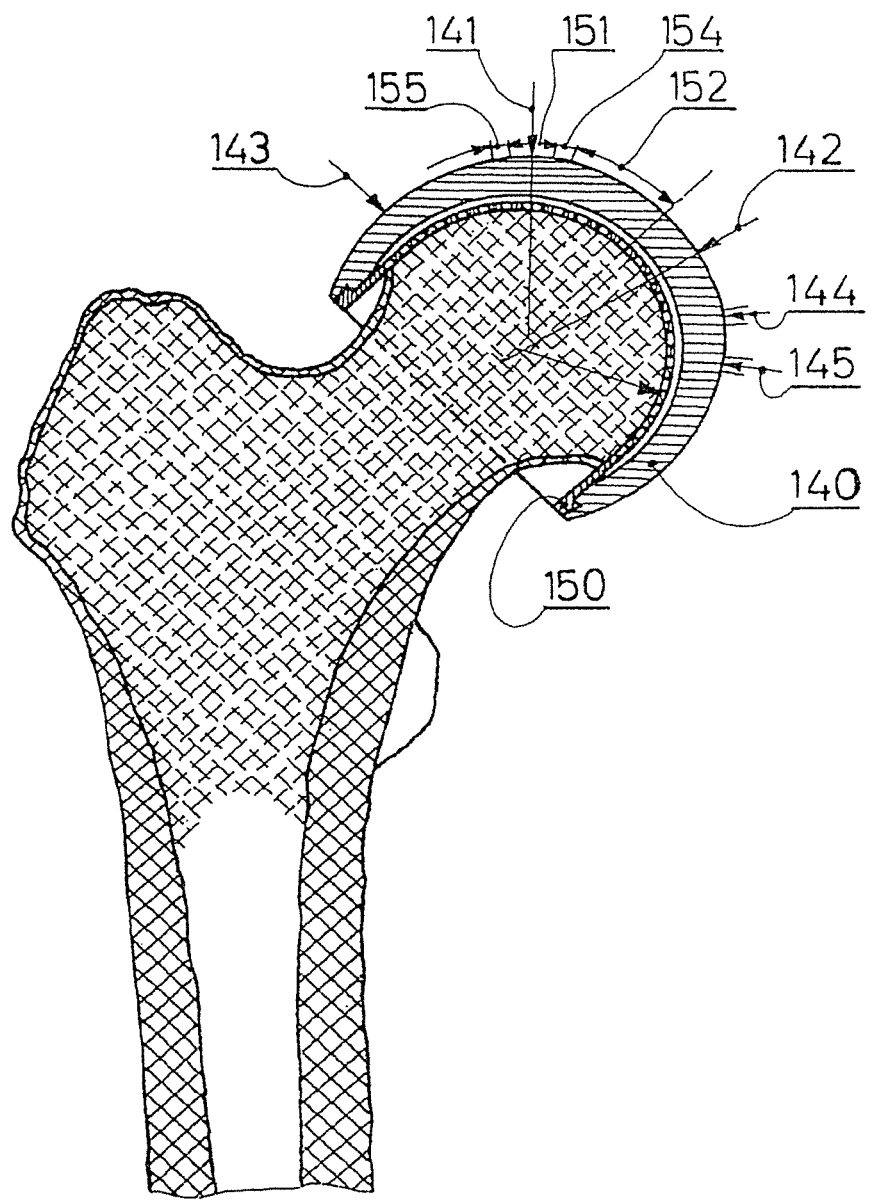
FIG. 12 is schematic cross sectional view of the femoral head resurfaced by the femoral head prosthesis with the perforated inner shell.

FIG. 12 shows a schematic cross sectional view of another embodiment of the invention, wherein the prosthetic head 140 is affixed to the femur via an inner, perforated shell 150, press-fitted onto the reamed head of the femur. For this fixation to work well, the bone of the femoral head needs to be in good condition, with good vascular supply, limiting the application to only a small subset of the patients. The prosthetic head is aspherical, the radius 141 over the band 151, closely matches the radius of the reamed acatabulum. The radius 142 over the polar region 152 is larger than the radius 141. The transition zone 154 has a small radius of curvature 144; the transition zone 155 the radius 145. The lower section of the prosthetic head 140 is also spherical with the radius 143 smaller than 141, to prevent jamming of the head in the acetabulum reamed out to the radius 102, see FIG. 9, which is the same as 141.

Double shell fixation of this type is the subject of the pending application WO/2005/094731, "Double shell implant for cementless anchorage of joint prostheses", by Slobodan Tepic and Henrik Malchau.

Figure 13:
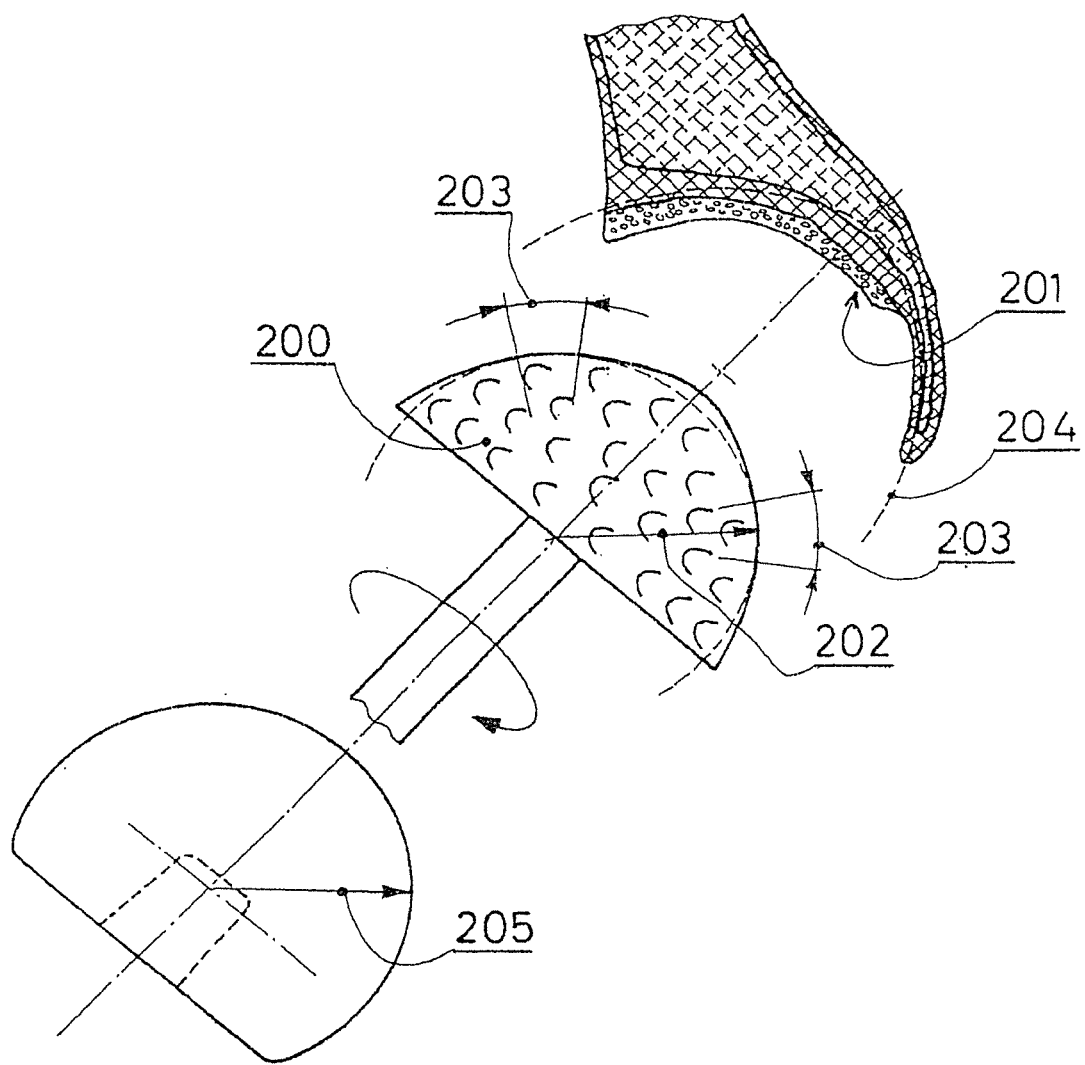
FIG. 13 is a schematic cross sectional view of the acetabulum a-spherically reamed to remove the surface layers of damaged cartilage and bone and to create a cavity for receiving the spherical head prosthesis.

FIG. 13 shows yet another embodiment of the invention, whereby the acetabulum is reamed to an aspherical shape, while the prosthetic head is spherical with the radius 205. The reamer 200 reams the acetabulum 201 to an exact contour 204 defined by the shape of the reamer. The radius 202 over a band 203 is equal to the radius 205 of the prosthetic head. At the pole, the reamer removes more bone than a spherical reamer would do. The same is true at the equator of the reamer. The contact to the prosthetic head is thus limited to the band 203.

Figure 14:
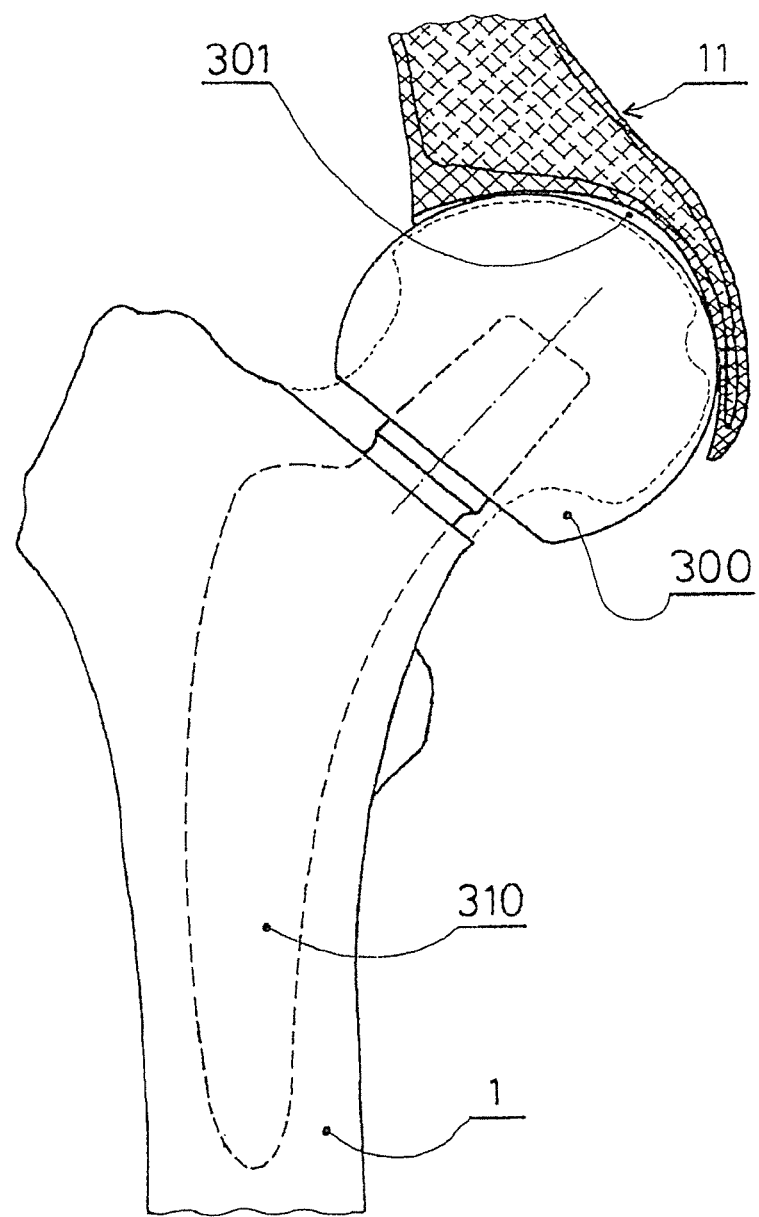
FIG. 14 is a schematic cross sectional view of the spherical femoral head prosthesis, affixed to a conventional femoral stem, articulating within the a-spherically reamed acetabulum.

FIG. 14 shows a perspective view of the proximal femur 1 with a spherical $_p$rosthetic head 300 affixed to the bone via a conventional stern 310. The acetabulum is shown in a cross sectional view of the pelvis 11, with a gap 301 formed between the articulating surfaces.

In all cases described, two essential conditions are met in order for the joint articulation according to the invention to function satisfactorily: (1) a gap in the area of otherwise maximal contact stresses within the articulation is provided for the purpose of supplying lubrication to the area of contact surrounding the gap, which is achieved by targeted congruency over a band of contact; (2) the surface of the prosthetic head which articulates against the reamed bone exhibits very low coefficient of friction, the preferred surface of the implant being amorphous diamond-like coating on a metallic substrate. Pyrolytic carbon is a costlier alternative.

The prosthetic femoral neck described is a preferred, novel solution for affixing the prosthetic head to the remaining bone of the femur. The transcortical concept allows approach to the dense cortical bone in the calcar region with a geometrically simple shape of the implant. The true and proven concept of threaded implants is extended by providing both external and internal threads to engage the bone for maximum stability without undue damage to the vascular supply of the involved bone.

The invention claimed is:

1. A partial hip prosthesis system, comprising
   (a) an articulation member, wherein said articulation member is spherical in shape and after implantation, allows for free rotation in a reamed acetabulum, and
   (b) an aspherical acetabulum reamer shaped to ream the bone of the acetabulum into an aspherical shape, so as to make, after implantation, an annular congruent band shaped contact to the articulation member which, after implantation, seals fluid in a gap between the articulation member and said reamed acetabulum,
   wherein the aspherical acetabulum reamer comprises a first radius, a second radius, a third radius, and a contour with a polar region and an equatorial region, wherein the first radius is located at the polar region, and the second radius is located at the equatorial region, and the third radius is located between the polar region and the equatorial region, wherein the third radius is equal to a radius of the articulation member, and a band of the aspherical acetabulum reamer having the third radius corresponds to the annular congruent band shaped contact, and wherein the first radius and the second radius are larger than the third radius.

2. A partial hip prosthesis system comprising
   (a) an articulation member, wherein said articulation member is spherical in shape and after implantation allows for free rotation in a reamed acetabulum, wherein a convex side of the articulation member is a prosthetic femoral head, and
   (b) an aspherical acetabulum reamer shaped to ream the bone of the acetabulum into an aspherical shape which contacts said prosthetic femoral head only at an annular congruent band, wherein a contour of the aspherical acetabulum reamer has a radius of curvature which is the same as that of a reamed acetabulum, and is centered about 30 to 55 degrees from the axis of revolution of the articulation member and its width is between 5 to 15 degrees, the radius of curvature corresponding to the annular congruent band shaped contact in the reamed acetabulum, wherein radii of curvature of the remaining contours of the aspherical acetabulum reamer are greater than the radius of the contour centered about 30 to 55 degrees from the axis of revolution of the articulation member.

3. A partial hip prosthesis system comprising
   (a) an articulation member, wherein said articulation member is spherical in shape and after implantation, allows for free rotation in a reamed acetabulum, wherein a convex side of the articulation member is a prosthetic femoral head, and (b) an aspherical acetabulum reamer shaped to ream the bone of the acetabulum into an aspherical shape so as to make, after implantation, an annular congruent band shaped contact to the articulation member, the annular congruent band shaped contact to the articulation member having a radius of curvature which is the same as that of a reamed acetabulum, and sealing, after implantation, fluid in a gap between the articulation member and said reamed acetabulum, wherein the aspherical acetabulum reamer comprises a first radius, a second radius, a third radius, and a contour with a polar region and an equatorial region, wherein the first radius is located at the polar region, the second radius is located at the equatorial region, and the third radius is located between the polar region and the equatorial region, wherein the third radius is equal to a radius of the prosthetic femoral head, wherein a band of the aspherical acetabulum reamer having the third radius corresponds to the annular congruent band shaped contact, and wherein the first radius and the second radius are larger than the third radius.

4. The partial hip prosthesis according to claim 1, wherein the prosthetic femoral head includes a diamond-like coating.

5. A partial hip prosthesis system comprising
(a) an articulation member, wherein a convex side of the articulation member is a prosthetic femoral head which has a first shape; and
(b) an acetabulum reamer shaped to ream the bone of the acetabulum into a shape which is different from said first shape, so as to make, after implantation, an annular congruent band shaped contact to the articulation member which, after implantation, seals fluid in a gap between the articulation member and a reamed acetabulum, wherein the annular congruent band shaped contact is centered about 30 to 55 degrees from the axis of revolution of the femoral head prosthesis, and its width is between 5 and 15 degrees of the femoral head prosthesis.

* * * * *